United States Patent
Chang et al.

(10) Patent No.: US 11,915,809 B2
(45) Date of Patent: *Feb. 27, 2024

(54) METHOD AND SYSTEM FOR AUTOMATICALLY GENERATING A SECTION IN A RADIOLOGY REPORT

(71) Applicant: RAD AI, Inc., Berkeley, CA (US)

(72) Inventors: Jeffrey Chang, Berkeley, CA (US);
Doktor Gurson, Berkeley, CA (US);
Eric Purdy, Berkeley, CA (US);
Brandon Duderstadt, Berkeley, CA (US); Jeffrey Snell, Berkeley, CA (US);
Andriy Mulyar, Berkeley, CA (US);
Deeptanshu Jha, Berkeley, CA (US)

(73) Assignee: RAD AI, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/207,880

(22) Filed: Jun. 9, 2023

(65) Prior Publication Data

US 2023/0343426 A1 Oct. 26, 2023

Related U.S. Application Data

(63) Continuation of application No. 17/725,031, filed on Apr. 20, 2022, which is a continuation of application
(Continued)

(51) Int. Cl.
*G16H 15/00* (2018.01)
*G16H 10/60* (2018.01)
(Continued)

(52) U.S. Cl.
CPC ............ *G16H 15/00* (2018.01); *G16H 10/60* (2018.01); *G16H 20/40* (2018.01); *G16H 40/63* (2018.01); *G16H 40/67* (2018.01); *G16H 50/20* (2018.01)

(58) Field of Classification Search
None
See application file for complete search history.

(56) References Cited

U.S. PATENT DOCUMENTS

| 10,127,662 B1 | 11/2018 | Reicher et al. |
| 10,140,421 B1 | 11/2018 | Bernard et al. |

(Continued)

FOREIGN PATENT DOCUMENTS

| CN | 111414464 A | 7/2020 |
| WO | 0239415 A2 | 5/2002 |
| WO | 2019025601 A1 | 2/2019 |

OTHER PUBLICATIONS

Chang, Jeffrey, et al., "Method and System for the Computer-Assisted Implementation of Radiology Recommendations", U.S. Appl. No. 18/215,354, filed Jun. 28, 2023.
(Continued)

*Primary Examiner* — Jason S Tiedeman
*Assistant Examiner* — Emily Huynh
(74) *Attorney, Agent, or Firm* — Jeffrey Schox; Caitlin Ploch

(57) ABSTRACT

A system 100 for automatically generating a field of a radiology report includes a set of one or more models. A method for automatically generating a field of a radiology report includes: receiving a radiologist identifier (radiologist ID); receiving a set of finding inputs; determining a context of each of the set of finding inputs; determining text associated with a portion or all of the radiology report based on the context and the radiologist style; and inserting the text into the report.

16 Claims, 8 Drawing Sheets

Related U.S. Application Data

No. 17/020,593, filed on Sep. 14, 2020, now Pat. No. 11,342,055.

(60) Provisional application No. 62/900,148, filed on Sep. 13, 2019.

(51) Int. Cl.
  *G16H 20/40* (2018.01)
  *G16H 40/63* (2018.01)
  *G16H 40/67* (2018.01)
  *G16H 50/20* (2018.01)

(56) References Cited

U.S. PATENT DOCUMENTS

| | | | |
|---|---|---|---|
| 11,342,055 | B2 | 5/2022 | Chang et al. |
| 11,610,667 | B2 | 3/2023 | Gurson et al. |
| 11,615,890 | B2 | 3/2023 | Chang et al. |
| 2007/0078679 | A1 | 4/2007 | Rose |
| 2010/0138239 | A1 | 6/2010 | Reicher et al. |
| 2013/0290031 | A1 | 10/2013 | Kay et al. |
| 2014/0379378 | A1 | 12/2014 | Cohen-Solal et al. |
| 2015/0112725 | A1 | 4/2015 | Ryan |
| 2015/0348229 | A1 | 12/2015 | Aguirre-Valencia et al. |
| 2016/0364862 | A1 | 12/2016 | Reicher et al. |
| 2018/0060533 | A1 | 3/2018 | Reicher et al. |
| 2018/0330828 | A1 | 11/2018 | Hayter |
| 2019/0021677 | A1 | 1/2019 | Grbic et al. |
| 2019/0122073 | A1 | 4/2019 | Ozdemir et al. |
| 2019/0139218 | A1 | 5/2019 | Song et al. |
| 2019/0362835 | A1* | 11/2019 | Sreenivasan ........... G06N 3/044 |
| 2020/0334416 | A1 | 10/2020 | Vianu et al. |
| 2020/0342967 | A1 | 10/2020 | Bronkalla et al. |
| 2021/0090694 | A1 | 3/2021 | Colley et al. |
| 2021/0110912 | A1 | 4/2021 | Mukherjee |
| 2021/0327596 | A1 | 10/2021 | Tahmasebi Maraghoosh et al. |

OTHER PUBLICATIONS

Dai, Ning, et al., "Style transformer: Unpaired text style transfer without disentangled latent representation", Ithaca: Cornell University Library, arXiv.org. (Year: 2019).
Ebesu, Travis Akira, "Deep learning for recommender systems", (Order No. 13900137). Available from ProQuest Dissertations & Theses Global. (2293976827). (Year: 2019).
Garud, Hrishkesh Deepak, et al., "Transforming human pose forecasting", (Order No. 27814956). Available from ProQuest Dissertations & Theses Global. (2399247743). (Year: 2019).
Jettaku, Amarin, et al., "Relation extraction between bacteria and biotopes from biomedical texts with X attention mechanisms and domain-specific contextual representations", BMC Bioinformatics, 20, 1-17, (2019).
Koncel-Kedziorski, Rik, et al., "Understanding and generating multi-sentence texts", (Order No. 13814316). Available from ProQuest Dissertations & Theses Global. (2305944561). (Year: 2019).
Lou, Robert, et al., "Automated detection of radiology reports that require u follow-up imaging using natural language processing feature engineering and machine learning classification", Journal of digital imaging, 33(1), 131-136. (Year: 2020).
Nandhakumar, Nidhin, et al., "Clinically Significant Information Extraction from Radiology Report", DocEng '17: Proceedings of the 2017 ACM Symposium on Document Engineering, Aug. 2017, pp. 153-162.
Sanjabi, Nima, "Abstractive text summarization with attention-based mechanism", (Projecte Final de Master Oficial). UPC, Facultat d'Informatica de Barcelona. (Year: 2018).
Song, Huan, "Data-driven representation learning in multimodal feature fusion", (Order No. 10838232). Available from ProQuest Dissertations & Theses Global. (2094858110). (Year: 2018).
Xue, Y., et al., "Multimodal Recurrent Model with Attention for Automated Radiology Report Generation", Medical Image Computing and Computer Assisted Intervention—MICCAI 2018. MICCAI 2018. Lecture Notes in Computer Science, vol. 11070. Springer, Cham. https://doi.org/10.1007/978-3-030-00928-1_52 (Year: 2018).
Zech, John, et al., "Natural Language-based Machine Learning Models for the Annotation of Clinical Radiology Reports", Radiology Reports. Jan. 30, 2018 (Jan. 30, 2018).
Zhang, Yuhao, et al., "Learning to Summarize Radiology Findings", Oct. 8, 2018 (Oct. 8, 2018). 1-20 [retrieved on Nov. 18, 2020].
"Improving and automating lung cancer screening", Nuance, Data Sheet, Nov. 2020, https://www.nuance.com/asset/en_us/collateral/healthcare/data-sheet/ds-powerscribe-lung-cancer-screening-en-us.pdf.
"Lung Cancer Orchestrator", Philips, first downloaded May 19, 2023, https://www.usa.philips.com/healthcare/product/HC841017/lung-cancer-orchestrator.
"Lung Cancer Screening", Eon Health, first downloaded May 19, 2023, https://eonhealth.com/lung-cancer-screening-software/.
"Radiology reports designed for patients", Scanslated, first downloaded May 19, 2023, https://scanslated.com.
"Merge Announces Release of Fusion PACS MX(TM) 3.0 Featuring Integrated Digital Mammography, and Release of Merge Mammo(TM) 7.10", Business Wire, May 19, 2008, p. NA. ProQuest. Web. Aug. 29, 2023. (Year: 2008).

\* cited by examiner

100

RADIOLOGY REPORT

Radiology organization code
Radiologist ID
Patient age

MRI of the brain

Clinical information

| Patient history. |

Comparison

| None. |

Findings

| Finding #1, Finding #2, Finding #3 |

Impression

| I |

Trigger: detection of cursor in last field

Time = $t_3$

FIGURE 3C

METHOD AND SYSTEM FOR AUTOMATICALLY GENERATING A SECTION IN A RADIOLOGY REPORT

CROSS-REFERENCE TO RELATED APPLICATIONS

This application is a continuation of U.S. application Ser. No. 17/725,031, filed 20 Apr. 2022, which is a continuation of U.S. application Ser. No. 17/020,593, filed 14 Sep. 2020, which claims the benefit of U.S. Provisional Application No. 62/900,148, filed 13 Sep. 2019, each of which is incorporated in its entirety by this reference.

TECHNICAL FIELD

This invention relates generally to the radiology field, and more specifically to a new and useful system and method for the automated generation of one or more sections of a radiology report in the radiology field.

BACKGROUND

Current radiology workflows are typically long and inefficient, requiring the radiologist to spend time and effort generating numerous fields within a radiology report. While automation of one or more fields can be implemented, the content and look of one or more fields of the report, such as the impression field, are typically highly dependent on the particular radiologist generating the report. Conventional attempts to automate these fields leave most radiologists dissatisfied with the results.

Thus, there is a need in the radiology field to create an improved system and method for automatically generating one or more fields of a radiology report in an accurate way which is also satisfactory to the particular radiologist generating the report.

BRIEF DESCRIPTION OF THE FIGURES

FIGS. 3A-3D depict a variation of a method for the automated generation of impression text in a radiology report.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
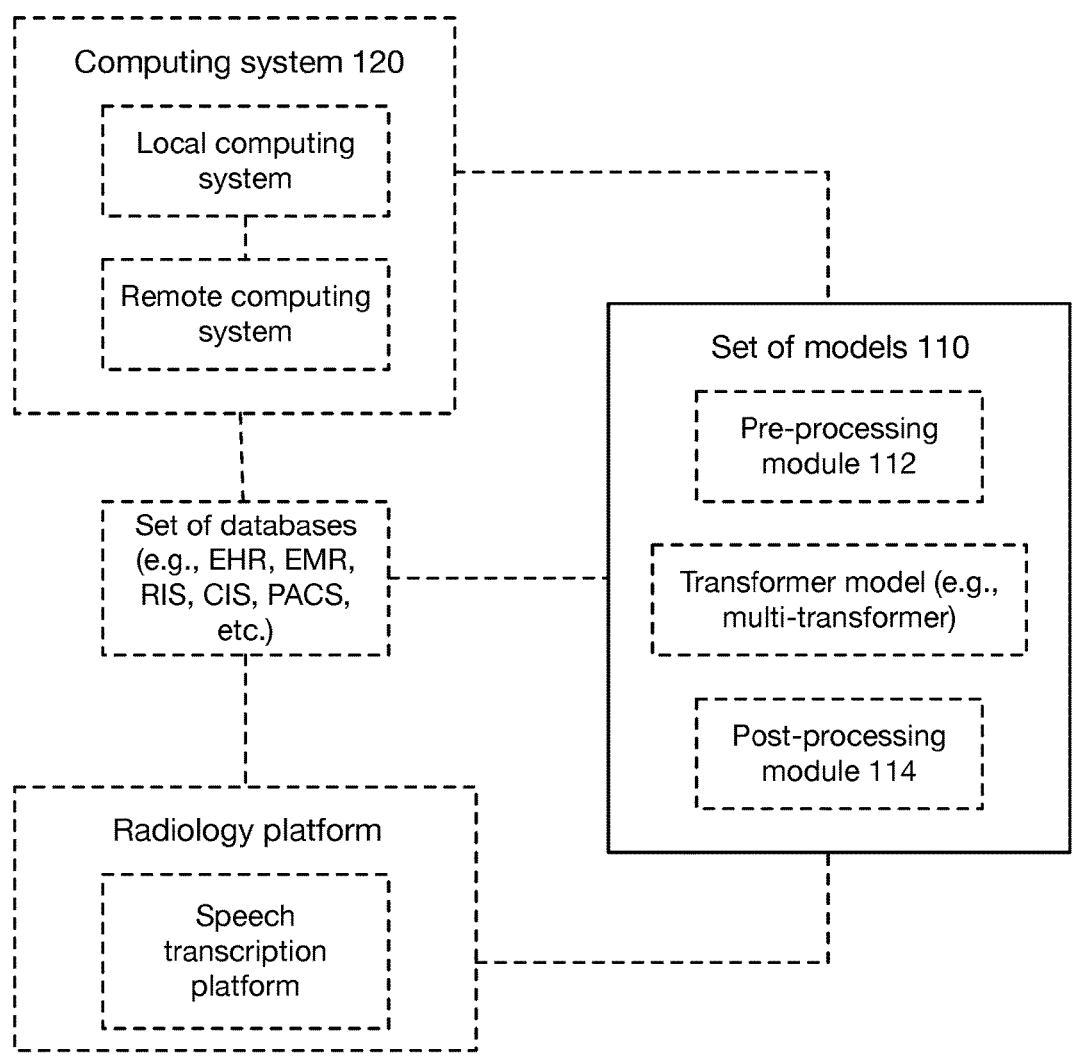
FIG. 1 is a schematic of a system for the automated generation of impression text in a radiology report.

As shown in FIG. 1, a system 100 for automatically generating a field (e.g., impression field) of a radiology report includes a set of one or more models 110. One or more of the set of models preferably includes a set of encoders and a set of decoders implemented in a machine learning model, such as a transformer machine learning model (e.g., multi-transformer model). Additionally or alternatively, the system can include and/or interface with any or all: of a pre-processing module 112, a post-processing module 114, a computing system 120 and/or processing system, a radiology platform such as one including a speech recognition platform, a set of devices (e.g., user devices), and/or any other suitable components or combination of components.

Further additionally or alternatively, the system 100 can include and/or interface with any or all of the systems, components, embodiments, and/or examples described in U.S. application Ser. No. 16/688,623, filed 19 Nov. 2019, which is incorporated herein in its entirety by this reference.

Figure 2:
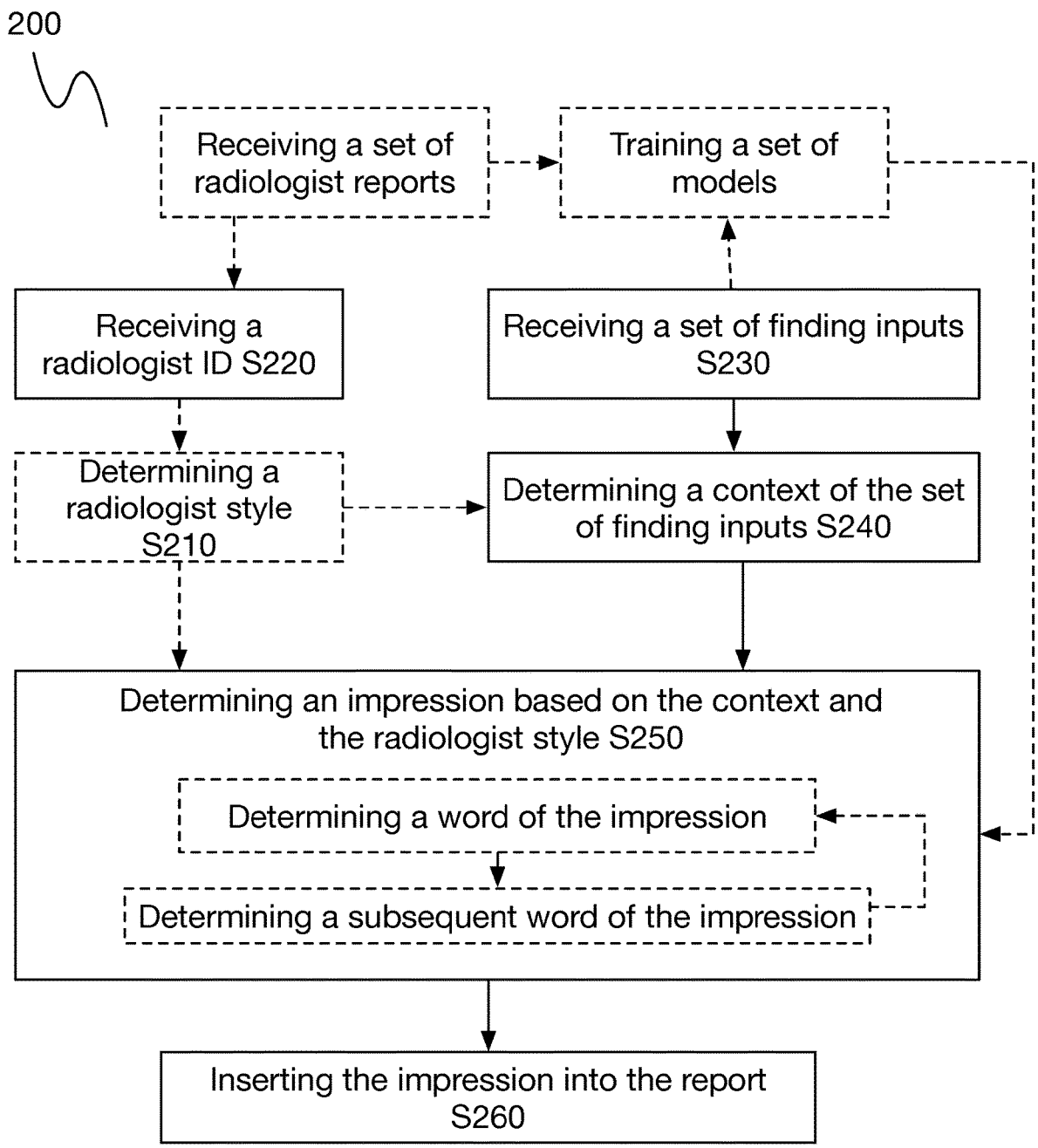
FIG. 2 is a schematic of a method for the automated generation of impression text in a radiology report.
Figure 3A:
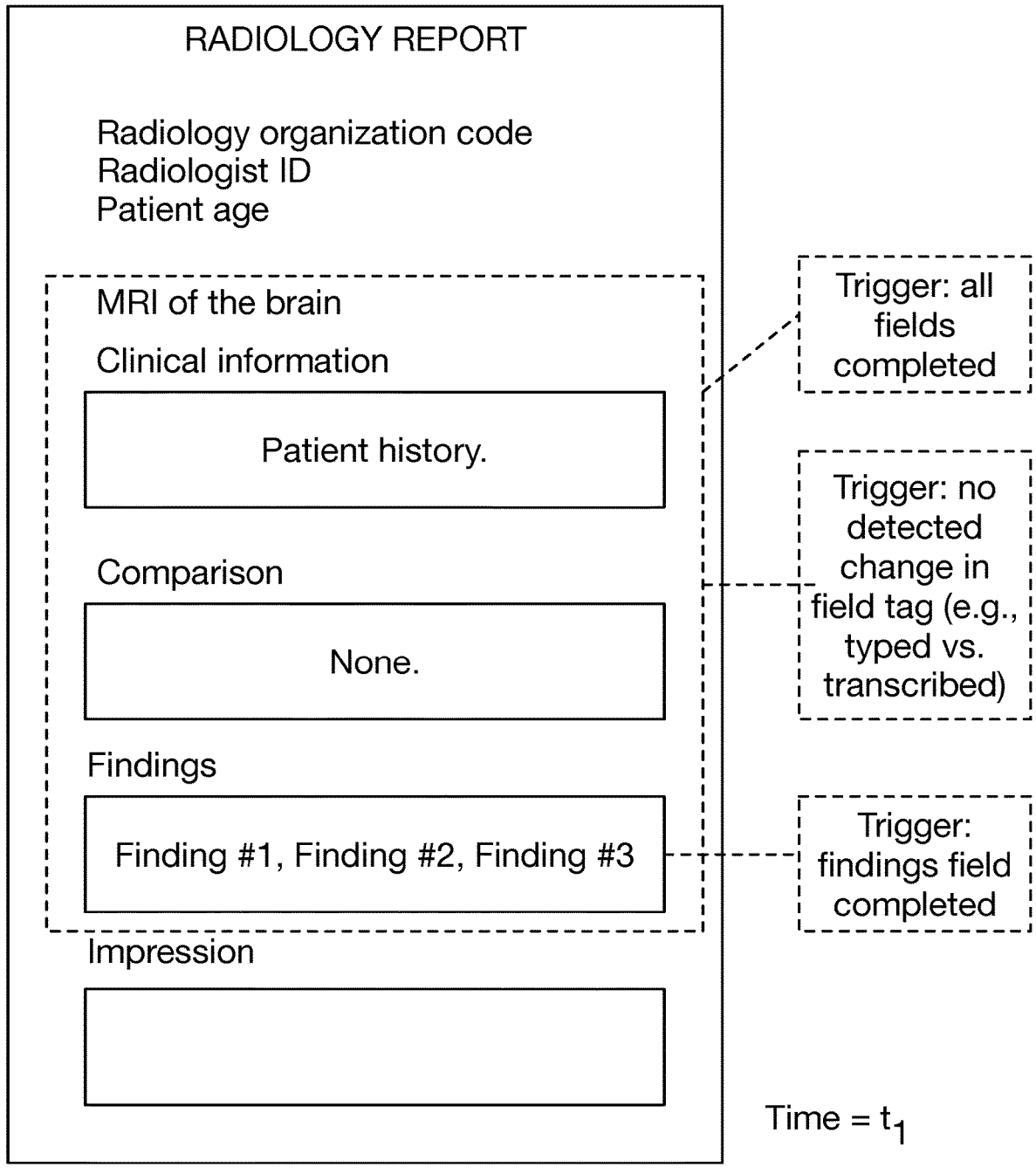
Figure 3B:
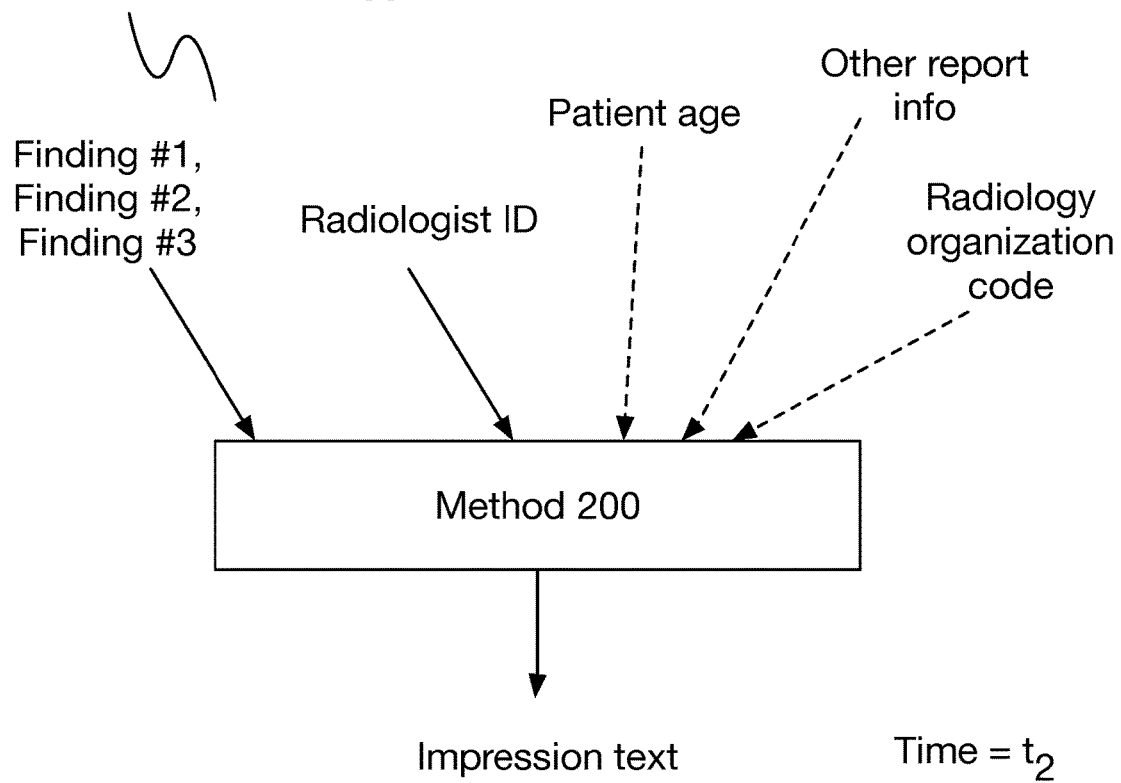
Figure 3D:
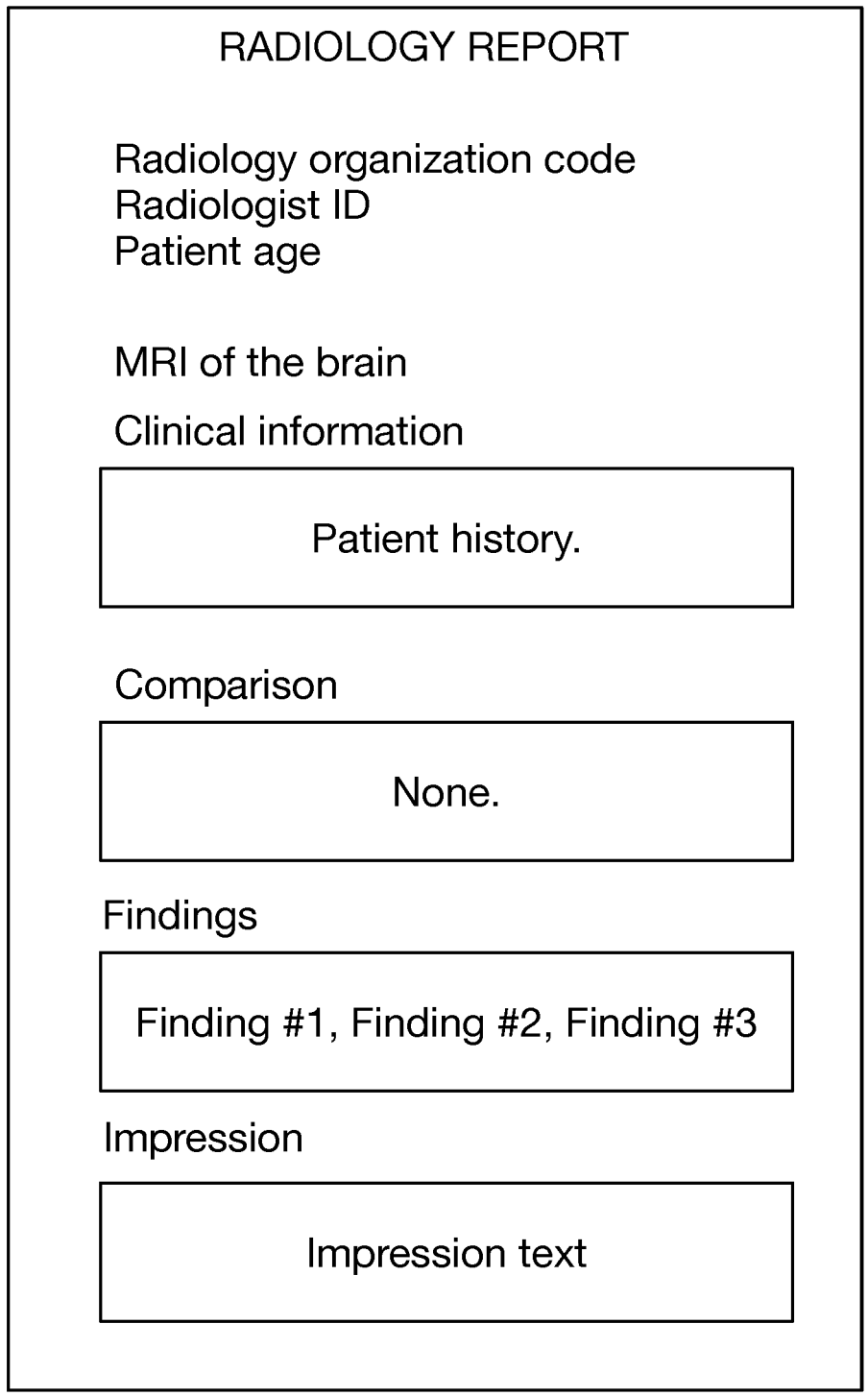

As shown in FIG. 2, a method 200 for automatically generating impression text (and/or any other suitable fields of a radiology report such as comparisons, contrast amounts, specific measurements, etc.) includes: receiving a radiologist identifier (radiologist ID); receiving a set of finding inputs and optionally other inputs; determining a context of each of the set of inputs; determining an impression based on the context and the radiologist style; and inserting the impression text (and/or any other suitable text) into the report. Additionally or alternatively, the method 200 can include any or all of: determining a radiologist style, training a set of models, preprocessing information, postprocessing information, and/or any other suitable processes performed in any suitable order.

Further additionally or alternatively, the method 200 can include and/or interface with any or all of the methods, processes, embodiments, and/or examples described in U.S. application Ser. No. 16/688,623, filed 19 Nov. 2019, which is incorporated herein in its entirety by this reference.

The method 200 can be performed with a system as described above and/or any other suitable system.

2. Benefits

The system and/or method can confer several benefits over current systems and methods.

In a first variation, the system and/or method confers the benefit of decreasing the time and/or effort required for a radiologist to generate a report by automatically generating an impression from at least a set of findings.

In a second variation, additional or alternative to those described above, the system and/or method confers the benefit of mimicking a radiologist's writing style (e.g., word choice, grammar, consolidation and summary of findings, style of conclusions drawn from summarized findings, preferred follow-up recommendations, etc.) in the automated generation of one or more sections of a radiology report. In a specific example, the method confers the benefit of high user adoption and satisfaction by producing an automated impression which closely mimics and/or matches an impression which would have been manually generated by the radiologist.

In a third variation, additional or alternative to those described above, the system and/or method confers the benefit of partially or fully standardizing any or all of the formatting and/or language of reports generated for a particular radiology group and/or healthcare facility, and of improving report recommendation adherence to consensus guidelines, billing and coding requirements, and/or quality metrics standards. In specific examples, for instance, one or more automated recommendations in an automated impression section of the report are configured to adhere to any or all of a set of preferences, requirements, standards, and/or guidelines.

In a fourth variation, additional or alternative to those described above, the system and/or method confers the benefit of enabling a zero-click generation of impressions without prematurely generating the impression.

Additionally or alternatively, the system and method can confer any other benefit.

3. System

The system 100 for the automated generation of a radiology impression (and/or any other suitable fields of a radiology report) includes a set of one or more models 110. Additionally or alternatively, the system can include and/or interface with any or all: of a pre-processing module 112, a post-processing module 114, a computing system 120, a radiology platform, and/or any other suitable components or combination of components.

The system 100 preferably functions to generate one or more fields of a radiology report, wherein the generated fields preferably include an impressions section of a radiology report. The system 100 further preferably functions to generate an impressions section which is similar to (e.g., imitates, mimics, replicates, approximates, etc.) in style and/or content the impressions that the radiologist manually generates and/or desires to generate.

Additionally or alternatively, the system 100 can function to generate an entire radiology report; facilitate compliance of a radiology report with one or more radiology standards and/or conventions (e.g., recommended language); increase and/or maintain an accuracy above a predetermined threshold of the generated impression; optimize a radiology report for healthcare facility billing and/or reimbursements; and/or perform any other functions.

3.1 System—Set of Models

The system 100 includes a set of models 110, which individually and/or collectively function to generate one or more fields of a radiology report which approximate the style of any or all of: a particular radiologist; an aggregated set of radiologists; an optimal standard for that field; and/or any other suitable entities. Additionally or alternatively, the set of models 110 can function to perform any or all of: decreasing a processing time and/or improving one or more processing parameters (e.g., increasing accuracy, increasing radiologist approval/satisfaction, decreasing radiologist edits to the generated fields, increasing detail of a generated radiology impression, increasing readability and/or interpretability of a generated field, etc.); increasing a quality or consistency of a radiology report; and/or performing any other suitable function(s).

The set of models are preferably located at (e.g., stored at, processed at, etc.) a computing system (e.g., as described above), further preferably a remote computing system (e.g., cloud computing system, remote server, etc.), but can additionally or alternatively be located at any or all of: a local computing system, a combination of computing systems, and/or at any other suitable location(s).

The set of models preferably includes one or more machine learning models, further preferably one or more deep learning models. Additionally or alternatively, the set of models can include any or all of: algorithms, equations, rules and/or rulesets, databases, lookup tables, and/or any other suitable tools for generating, checking, editing, and/or otherwise processing language information in a radiology report.

The set of models receives a set of inputs, wherein the set of inputs preferably includes at least a radiologist ID (e.g., as described below), which functions to specify a particular radiologist's style with which to generate a radiology report field (e.g., impressions section), and a set of finding inputs (e.g., as described below), such as the contents (e.g., sentences) of a findings field of the radiologist report. The set of inputs further preferably includes a clinical indication(s) section of the radiology report and optionally a report title, technique, and/or set of comparison studies. Further additionally or alternatively, the set of inputs can include any other sections of the report, other radiologist information, other patient information (e.g., from the radiology report, from outside of the radiology report, from a historical radiology report, etc.), healthcare facility information, database information (e.g., from an EHR database, from an EMR database, from a PACS database, from a RIS database, etc.), radiology group information, radiology standards, billing procedures and/or guidelines, and/or any other information from any suitable sources.

The set of finding inputs are preferably received from a speech recognition platform, wherein the radiologist verbally dictates information (e.g., the set of findings, information which is used to determine the set of findings, etc.) which is transcribed by the speech recognition platform into text. Additionally or alternatively, the set of finding inputs can be any or all of: received from the radiology report (e.g., already transcribed from a speech recognition platform, typed and/or written by a radiologist, etc.); received from a database, storage, and/or server; received as an output from a model (e.g., predicted with a machine learning model); and/or otherwise determined and/or received. The radiologist ID is preferably associated with (e.g., references and/or retrieves from remote storage, from local storage, from a database, from a remote server, from a cloud computing system, etc.) a radiologist style matrix and/or vector (e.g., as described below) which within the model(s) to help produce an impression which mimics the style of the particular radiologist. The radiologist style matrix is preferably part of the architecture of one or more models (e.g., as described below), but can additionally or alternatively be used as an input into one or more models (e.g., retrieved from a lookup table based on the radiologist ID and used as an input to a transformer model). Further additionally or alternatively, the radiologist style can be represented in any other suitable form (e.g., set of weights, set of parameters, etc.), include any suitable information (e.g., aggregated style of a set of radiologists, optimal style of a theoretical radiologist, optimal style for a radiology group and/or healthcare facility and/or compliance with a set of radiology standards, etc.), and/or used in the model(s) in any suitable ways.

Additionally or alternatively, the set of models can receive any suitable information as inputs, such as any or all of: any information from a radiology report (e.g., the entire radiology report, any section from the radiology report, patient metadata, radiologist information, healthcare facility information, radiology group information, etc.); any information from other radiology reports (e.g., prior report(s) of the patient); information from a database, storage, server, and/or software tools (e.g., EMR database, EHR database, RIS, CIS, PACS, etc.); a set of images (e.g., diagnostic images of the patient); video; and/or any suitable information.

The set of models preferably includes one or more neural networks (e.g., feedforward neural networks, recurrent neural networks, convolutional neural networks, etc.), but can additionally or alternatively include any suitable algorithms (e.g., machine learning algorithms), decision trees, models, and/or any other suitable processing tools. The models can be trained through supervised learning (e.g., based on annotated reports, based on manually generated reports, based on synthesized reports, etc.), trained through unsupervised learning, untrained, or otherwise determined.

The set of models further preferably includes one or more deep learning models configured for natural language processing (NLP) (e.g., models configured to handle sequential data), such as one or more deep learning models with attention mechanisms, such as any or all of: a sequence-to-sequence architecture; one or more attention layers (e.g., in one or more encoders, in one or more decoders, etc.); one or more self-attention layers (e.g., in one or more encoders, in one or more decoders, etc.); and/or any other tools, features, and/or architecture. Additionally or alternatively, the deep learning model(s) can be configured for any suitable applications and/or otherwise designed.

The set of models preferably includes models implementing parallelization (e.g., processing all tokens at the same time) wherein processing data in order is not required, which can function to reduce training times and processing times. In preferred variations, for instance, the set of models includes a set of one or more transformers. In specific examples, for instance, the set of models includes a transformer model including multiple encoders with one or more decoders that each consult one or more of the encoders sequentially. In a particular example, the set of models includes a transformer model (equivalently referred to herein as a multi-transformer model) with multiple decoders that each consult a set of multiple encoders in a sequential fashion. Additionally or alternatively, the set of models can include any other suitable transformers and/or transformer systems (e.g., Bidirectional Encoder Representations from Transformers [BERT], Generative Pre-Trained Transformer [GPT], etc.); a transformer with any suitable number and/or arrangement of encoders and decoders (e.g., equal number of encoders and decoders, more encoders than decoders, more decoders than encoders, each decoder consulting one or more of the encoders in varying order, a single encoder, a single decoder, etc.); a single transformer; multiple transformers; and/or any other suitable transformers or models.

Additionally or alternatively, the set of models can include other NLP models such as recurrent neural networks (RNNs) (e.g., long short-term memory [LSTM] models, gated recurrent units [GRUs], etc.) and/or any other suitable models.

The model(s) can be any or all of: trained, pretrained, fine-tuned or using other forms of transfer learning (e.g., based on a pretrained model), combined with one or more ontologies (e.g., radiological or other clinical ontology database), and/or any combination of these. In some variations, for instance, the set of models includes one or more trained and/or pretrained models which are fine-tuned based on radiology report language.

The set of models 110 can optionally include and/or interface with a pre-processing module 112, which functions to clean up and/or otherwise modify data prior to training on and/or processing it. The pre-processing module 112 is preferably implemented prior to or during the training of the model(s), but can additionally or alternatively be implemented on data serving as input to the trained model, and/or be implemented at any suitable time(s) during the method 200 in any suitable way(s).

The set of models 110 can optionally include and/or interface with a post-processing module 114, which functions to edit and/or otherwise modify one or more outputs produced by the set of models. This can include any or all of: formatting an output (e.g., an impressions section); further improving language styling to better match the style of the radiologist; checking and/or adjusting language for compliance with recommended and/or required language (e.g., medical classification lists such as the International Classification of Diseases and Related Health Problems [ICD], ICD-10, usage of word "indicates" for diagnoses to conform with billing guidelines and/or requirements, merit-based incentive payment system [MIPS] to help with and/or maximize reimbursement, etc.); notifying the radiologist of language which potentially may not conform with recommended and/or required language (e.g., as described above, so that the radiologist may manually edit, etc.); and/or any other processing. Additionally or alternatively, any or all of the above can be performed in pre-processing, with the set of models 110, and/or at any suitable time(s) during the method 200 with any suitable models and/or modules.

Any or all of the set of models 110, pre-processing module, and post-processing module can be configured according to the type of imaging (e.g., X-ray, MRI, CT, ultrasound, etc.) associated with the radiology report. The type of imaging, for instance, can be associated with any or all of: different report templates that need to be removed or modified in pre-processing; different styles and/or content of impressions (e.g., no further imaging recommendations for certain findings on MRI reports because it is already the gold standard for imaging those findings, different conditions and/or pathologies being investigated, etc.); different formatting; and/or any other differences. Additionally or alternatively, the models can be otherwise configured based on any other suitable features and/or information.

In a first variation, the set of models includes one or more transformers (e.g., multi-transformer), which receive at least a radiologist ID and/or radiologist style matrix, along with a transcribed findings section of a radiologist report as inputs, wherein the one or more transformers produce an impressions section which mimics the radiologist's style and accurately assesses the findings. The set of models further preferably receives as an input a clinical indication(s) section from the radiology report, and optionally any or all of: the report title, technique section (e.g., how the exam was performed and whether contrast was used in the imaging), comparison information (e.g., comparison section of report, list of comparison studies, etc.), and/or any other suitable information.

Figure 4:
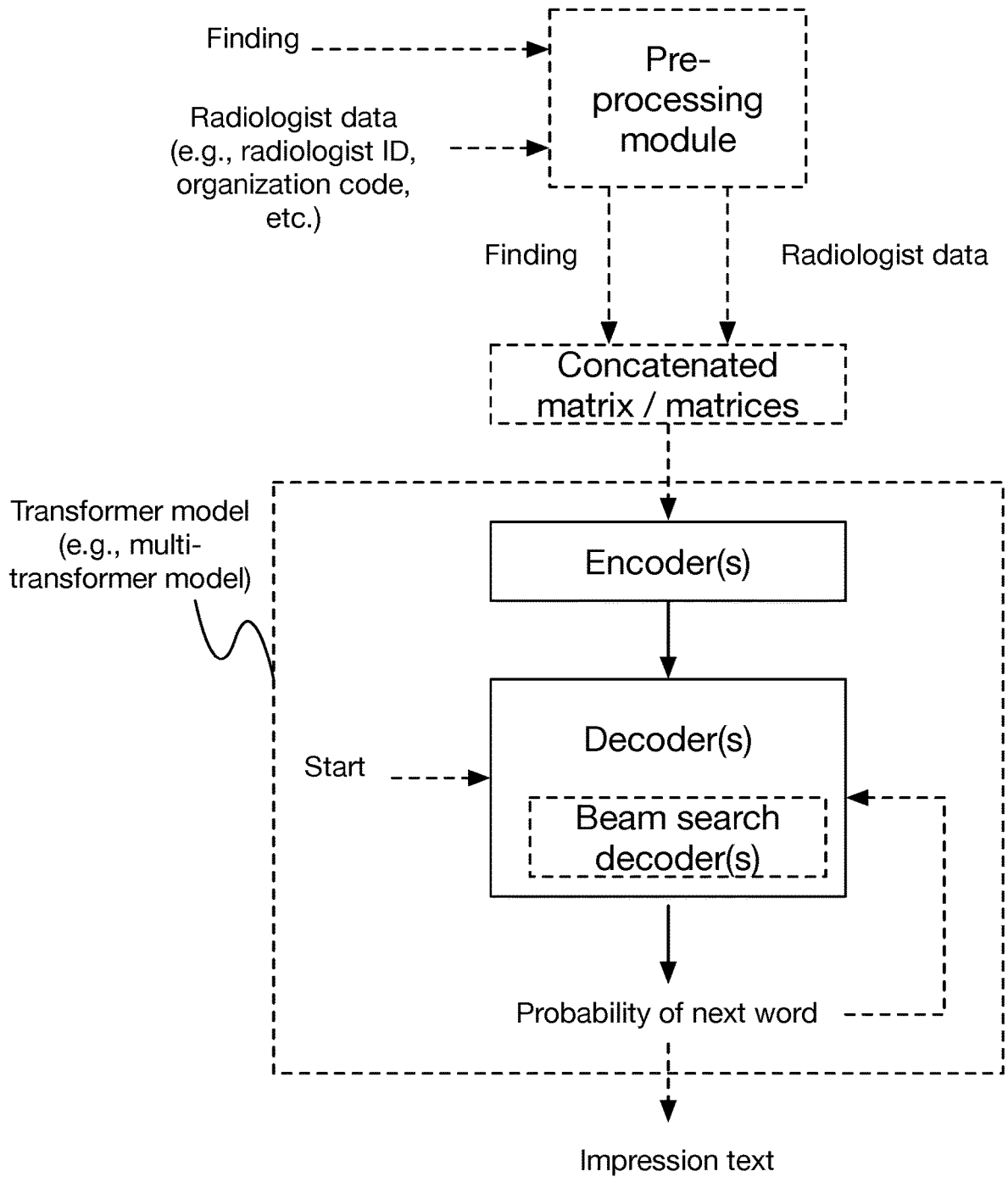
FIG. 4 depicts a schematic variation of a system for the automated generation of impression text in a radiology report.

In specific examples (e.g., as shown in FIG. 4), the system 100 includes at least one transformer model, wherein the transformer model includes a set of encoders and a set of decoders (e.g., beam search decoders) configured to determine a string of impression text based on at least a radiologist ID and one or more sections (e.g., findings section) of a radiology report.

3.2 System—Computing System 120

The system 100 can include and/or interface with a computing system 120, which functions to implement the set of models. Additionally or alternatively, the computing system can function to store one or more models and/or information, train one or more models, pre-process information, post-process information, and/or perform any other suitable functions.

The computing system can include and/or interface with any or all of: a processing system (e.g., set of processors, set of microprocessors, CPUs, GPUs, etc.), storage, memory, software programs/tools (e.g., radiology software, a speech recognition platform, etc.), and/or any other suitable components.

The computing system is preferably at least partially arranged remotely, but can additionally or alternatively be arranged locally (e.g., at a healthcare facility, at a radiologist's workstation, etc.), at a device (e.g., mobile device, stationary device, etc.) and/or among multiple devices, and/or at any suitable locations.

In a first variation, the set of models 110 are processed at a remote computing system, wherein the remote computing system interfaces with a radiology platform (e.g., as described below), wherein the computing system receives one or more of a set of inputs from the radiology platform (e.g., findings) and transmits a generated impression to the radiology platform to be integrated into the radiology report.

3.3 System—Radiology Platform

The system 100 is preferably configured to interface with a radiology platform (e.g., radiology reporting platform, PowerScribe, Fluency for Imaging, etc.), wherein the radiology platform preferably includes and/or interfaces with a speech recognition system which is equivalently referred to herein as any or all of: a speech recognition platform, a speech transcription system and/or platform, a voice recognition system and/or platform, a voice transcription system and/or platform, a speech-to-text system and/or platform, and/or any other suitable platform including any suitable tools and/or programs.

Additionally or alternatively, the system 100 can include and/or be configured to interface with any or all of: a Picture Archiving and Communication System (PACS) and/or alternative image viewing and image storage platform, a voice recognition platform, an intelligent radiology worklist and/or alternative radiology worklist, a Radiology Information System (RIS) and/or alternative patient tracking platform, an electronic medical record (EMR) database, an electronic health record (EHR) database, a Clinical Information System (CIS) platform and/or alternative management software, a Health Information System (HIS) platform and/or alternative management software, a Laboratory Information System (LIS) platform and/or alternative management software, one or more vendor-neutral archive (VNA) components, and/or any other suitable components. The system 100 can optionally be tailored to the preferences of a particular radiology group, tailored to the preferences of multiple radiology groups, agnostic of radiology group preferences, tailored to the preferences of an individual radiologist and/or aggregated set of radiologists, and/or otherwise configured.

In a preferred set of variations, the system 100 is configured to interface with (e.g., integrate with, communicate with, be built on top of, as a virtual machine, etc.) a radiology platform including a speech recognition platform, wherein the method 200 is adapted to integrate with the features of the particular radiology platform (e.g., hotkeys, radiology report formatting, inclusion or removal of specific language in the report dependent on adjustable configuration(s), varying placement of caret (e.g., cursor) or selection of text after generation of impression, variations in user interface, user notifications, options for collecting user feedback, etc.).

In additional or alternative variations, the system 100 includes any or all of the radiology platform and/or a corresponding method 200 can be otherwise suitably integrated with a radiology platform.

4. Method

As shown in FIG. 2, a method 200 for automatically generating impression text (and/or any other suitable fields of a radiology report such as comparisons, contrast amounts, specific measurements, etc.) includes: receiving a radiologist identifier (radiologist ID); receiving a set of finding inputs; determining a context of each of the set of finding inputs; determining an impression based on the context and the radiologist style; and inserting the impression text (and/or any other suitable text) into the report. Additionally or alternatively, the method 200 can include any or all of: determining a radiologist style, training a set of models, preprocessing information, postprocessing information, receiving other inputs (e.g., worklist, PACS information, RIS information, HIS information, EHR and/or EMR information, etc.), and/or any other suitable processes performed in any suitable order.

The method 200 functions to generate an automated impression from a set of radiology findings and within the style of a particular radiologist. Additionally or alternatively, the method 200 can function to generate any suitable portion or all of a radiology report, reduce the time and/or effort required to generate a radiology report, learn a radiologist's particular style of writing and/or dictating impressions and/or findings, increase and/or maintain accuracy of an impressions and/or findings section, enable compliance with and/or optimization of one or more healthcare facility and/or radiology organization standards, and/or perform any other suitable function(s).

An impression herein refers to an impression of a radiology report, which conventionally uses the findings (and/or any or all of the patient clinical history, indication for the imaging study, etc.) to summarize a patient condition (e.g., provide a diagnosis and/or summarize the findings) and/or otherwise summarize the state of the patient (e.g., recommend and/or prescribe a follow-up for the patient and/or a particular disease state, posit one or more potential disease states, etc.). Because the impression section typically offers critical information for decision-making, it is conventionally considered to be the most important and/or personalized part of the radiology report.

The findings section conventionally lists the radiologist's observations and findings regarding a set of one or more areas of the body examined in an imaging study (e.g., computed tomography [CT] imaging, magnetic resonance imaging [MRI], ultrasound imaging, radiography, etc.). The radiologist can indicate whether each area was found to be normal, abnormal or potentially abnormal. Sometimes an area of the body is included and can be evaluated using the images, but is not discussed. This situation typically means that the radiologist did not find the area noteworthy for comment.

The method 200 is preferably configured to be integrated within a standard radiology workflow, but can additionally or alternatively be configured to replace one or more processes in a standard radiology workflow, be performed independently of a standard radiology workflow, and/or be otherwise performed.

The method 200 is preferably performed with a set of models (e.g., as described above) and/or any suitable neural network architecture. The set of models are preferably trained such that the set of models jointly learns how to structure an impression from a finding and how a radiologist style (e.g., as defined as a matrix of coefficients) would interact with that impression, but can additionally or alternatively be otherwise configured.

Generating an impression is preferably fully automated but can additionally or alternatively be partially manually generated (e.g., require portions to be manually entered, enable edits to be manually entered, provide multiple options for generated impression language and/or additional or alternative language that the user can optionally select or deselect, etc.), and/or be otherwise determined.

4.1 Method—Training the Set of Models S205

The method 200 can optionally include training the set of models S205, which functions to train any or all of the set of models 110 used to determine the impression section.

The set of models can be trained with any or all of: supervised learning, semi-supervised learning, unsupervised learning, and/or any other suitable training processes. Training the models can additionally or alternatively include fine tuning one or more models (e.g., pretrained models) with radiology report data. Further additionally or alternatively, the method 200 can implement already trained models and/or any other suitable models and/or algorithms.

The method 200 can additionally or alternatively include one or more preprocessing processes, such as preprocessing information used to train one or more models.

Preprocessing information can optionally include removing or modifying one or more false positives from training data when training the set of models (e.g., during initial training, during a second and/or iterative training, during a fine-tuning process, etc.), which can function to: make the system and/or method more robust in determining an accurate impression, prevent and/or minimize machine learning hallucinations, and/or perform any other function(s). In some radiology reports, for instance, the findings section does not include a particular finding which the impression section does include. In a specific example, a radiologist does not mention anything about the enlarged size of the patient's heart in the findings section but then realizes it at the last minute and includes it only in the impression section. This may also include removing or modifying one or more word or phrase repeats, comments not found within the findings, templated text, or macro text from the impression section. Removing or modifying false positives from the training data can function to help prevent the system from inserting these "non-finding" impressions randomly and/or when not warranted/relevant.

Additionally or alternatively, preprocessing can include removing or modifying training data corresponding to false negatives, such as radiology reports in which a clinically significant finding is mentioned but not commented on in the impression section, or reports in which measurements and/or other language is swapped between or among two or more distinct findings, and/or any other suitable data.

Preprocessing can optionally additionally or alternatively include adding and/or removing items from training data (e.g., using a syntheticator), which can include any or all of: training the model(s) to add phrasing and/or use particular language which is recommended and/or prescribed (e.g., based on standards of a radiology society and/or group, based on preferences of a radiology group, based on preferences of a particular radiologist, based on preferences of a healthcare facility for coding and/or billing optimization and/or to satisfy coding and/or billing requirements or standards, etc.); training the model(s) to not use phrasing that is recommended against; add, remove, and/or edit formatting from radiology reports used as training data (e.g., remove call reports, signatures, and/or other templated text); and/or add or remove any other items, words, phrases, or sentences (e.g., including any form of data perturbation). In a specific example, for a particular radiology group, for instance, it may be good practice in cases of rib trauma with chest pain or tenderness to say whether or not there are displaced rib fractures in a chest X-ray. In these cases, the method 200 can optionally include correcting trauma chest X-ray training data for this radiology group and/or others which does not mention this.

Preprocessing can optionally additionally or alternatively include upweighting or upsampling sets of cases in the training data, which can function to help the model(s) properly handle complex and/or particularly important (e.g., critical, life-threatening, etc.) cases. In some variations, for instance, the method 200 includes implementing a loss function to upweight cases so that model pays closer attention to them. In specific examples, cancer cases, which are complicated to interpret and determine accurate impressions for, are upweighted through a loss function. In other variations, for instance, the method 200 includes upsampling of such complex cases.

Preprocessing can optionally additionally or alternatively include implementing subword vocabulary embeddings.

Preprocessing can optionally additionally or alternatively include tokenizing one or more recommendations, which functions to increase the processing speed. In some variations, for instance, preprocessing includes replacing a relatively long string of text in the radiology report (e.g., in the impression section, in any section of the radiology report, etc.) with a particular token representing the replacement and indicating in post-processing that the token should be reverted back to the original string, a variation of the original string, or the associated or unassociated output from one or more models or other predictive modeling or algorithm(s) (e.g., machine learning algorithms) specific to one or more recommendations. This can additionally or alternatively performed with the models themselves (e.g., later in the method 200), wherein one or more models are trained specifically to one or more types of recommendations, which is used to select the appropriate consensus guideline recommendation as an output in an automatically generated radiology impression. The language of these recommendations can be manually or automatically updated as consensus guidelines change, and may also be modified by or for specific radiology groups, specific health systems or hospitals, and/or individual radiologists.

Preprocessing can optionally additionally or alternatively include training separate models based on a set of preferences (e.g., preferred and/or prescribed recommendations, radiology group preferences, radiologist preferences, healthcare facility preferences, preferred follow-up treatments, etc.). In some variations, for instance, models are trained separately to be able to determine particular recommendations based on the patient's condition (e.g., as determined in the findings). These recommendations can be any or all of: guided by radiologist advisors and/or societies; guided by publications and/or flowcharts; guided by collaborative care team decisions on follow-up treatment; and/or any other suitable information. Additionally or alternatively, the models can be trained to reflect recommendations which often get updated. In some variations, for instance, the recommendation data being trained on is historical, wherein the method includes tagging that recommendation and updating it and/or flagging it so that it can be updated. In specific examples, a token is used to tag a portion of the impression (e.g., corresponding to outdated and/or potentially outdated information) when training the model, wherein in post-processing, logic adjusts the language corresponding to the token to reflect the up-to-date language.

The method 200 can additionally or alternatively include any other preprocessing or combination of preprocessing processes; be performed in absence of preprocessing; include preprocessing at other times in the method 200; and/or be otherwise performed.

The method 200 can optionally include any number of postprocessing processes (e.g., to postprocess data after being processed by the set of models), such as any or all of those described above and/or any other suitable processes. Alternatively, the method 200 can be performed in absence of postprocessing.

In some variations, for instance, postprocessing can include automatically marking (e.g., highlighting, providing a notification associated with, etc.) and/or changing language in an automatically or partially automatically generated section (e.g., impression field) of the radiology report.

Additionally or alternatively, this can be performed during processing with the model(s), during preprocessing, multiples times throughout the method, and/or at any suitable time(s).

This can function to achieve any or all of the functions described above (e.g., compliance with radiologist standards or preference, billing requirements, etc.) and/or any other suitable function(s). In some examples, for instance, the language used in one or more portions of generated text (e.g., as part of an automatically generated impression section) can be automatically changed (e.g., at the time of generation, in postprocessing, etc.) and optionally mentioned in one or more notifications to the radiologist (e.g., depending on the type of change) as to why the change was made (e.g., and requiring no further action from the radiologist, to receive confirmation from the radiologist, to receive an edit and/or a rejection of the change from the radiologist, etc.). Additionally or alternatively, the text can be automatically highlighted and/or otherwise marked, wherein the highlighted portion includes language suggested to the radiologist to be changed (e.g., to optimize one or more of: billing, reimbursement, and compliance with a set of radiology standards), and optionally requiring an input from the radiologist to change.

Additionally or alternatively, S205 can include any other suitable processes.

4.2 Method—Determining a Radiologist Style S210

The method 200 optionally includes determining a radiologist style S210, which functions to characterize any or all of the preferences, tendencies, idiosyncrasies, writing styles, summary writing styles, grammar, and/or any other characteristics of the radiologist when writing a radiologist report (e.g., impression section). The radiologist style is preferably specific to a particular radiologist, but can additionally or alternatively be specific to a particular radiology group (e.g., to conform to a set of report requirements established by the radiology group), a particular healthcare facility, and/or any other entity.

The radiologist style can be used to determine any or all of: a length of one or more sections of the radiology report (e.g., length of an impression section), a brevity of one or more section(s), a word flow, a type (e.g., formal versus informal, difficulty level, language, etc.) of words used in one or more sections of the radiology report, a subset of words typically chosen by the radiologist (e.g., a set of words routinely chosen by the radiologist over their respective synonyms, a set of words having been chosen previously by the radiologist, etc.), an ordering and/or prioritization of a set of findings, a summarization of a set of multiple findings (e.g., order in which multiple findings are listed, which findings are grouped into more general findings, which findings are included in the impression and which are not, etc.), pertinent negative and/or global negative language (e.g., language that describes the lack of specific relevant positive findings and/or general positive findings), the conclusion(s) generated from a set of findings such as radiologist-specific requirements for predicting a patient condition (e.g., radiologist only characterizes a spine curvature as scoliosis if it has an angle of 10 degrees or greater), differential diagnoses generated from a set of findings (e.g., indicating that any of these three patient conditions could result in this set of findings, and potentially discussing or explaining why one or more of these patient conditions is considered more or less likely), and/or any other suitable feature of the section(s) of the radiology report.

The radiologist style is preferably determined based at least in part on data from radiology reports previously generated (e.g., manually generated) by the radiologist. Additionally or alternatively, the radiologist style can be determined based on other radiologist inputs (e.g., collected in surveys, questionnaires, etc.), predicted or synthetic data (e.g., synthetic radiology reports approved by the radiologist, etc.), radiologist metadata (e.g., demographic information, experience level, etc.), radiology group information, and/or any other suitable information.

The radiologist style is preferably in the form of a mapping (e.g., matrix, vector, auxiliary field of another matrix such as a set of word embeddings, etc.) including a set of weights to be used in subsequent process(es) of the method to generate an impression and/or any other suitable section(s) of a radiology report, but can additionally or alternatively include any other data in any suitable data format. The radiologist style is preferably determined through deep learning, such as through any or all of: a set of trained models, a set of algorithms (e.g., machine learning algorithms), a set of neural networks, and/or any other suitable deep learning infrastructure. Additionally or alternatively, the radiologist style can be determined manually and/or through any other suitable process(es).

S210 is preferably performed once for each radiologist during an onboarding of the radiologist into the system 100. Additionally or alternatively, S210 can be performed once a radiologist has manually generated a predetermined number of reports, completed a predetermined number of studies, achieved a certain level of experience, and/or based on any other milestone. Further additionally or alternatively, S210 can be performed multiple times (e.g., every time the method 200 is performed, when a radiologist style is updated, when training one or more machine learning models, when using one or more radiologist edits made to generated impressions as training data for reinforcement learning, upon the generation of a new report, based on radiologist prompting, based on radiology group prompting, once a predetermined amount of time has passed, at a predetermined frequency, etc.), and/or at any other time(s).

The radiologist style can be determined based on any or all of: a set of models (e.g., machine learning models, any or all of the set of models 110, etc.); one or more algorithms; manually; and/or based on any other processes.

In a first variation, S210 includes determining a radiologist style vector with a trained model based on a set of (e.g., hundreds of, at least 100, etc.) radiology reports previously manually generated by the radiologist, wherein the radiologist style vector is subsequently used in method to automatically generate impression text of a radiologist report.

4.3 Method—Receiving a Radiologist Identifier (Radiologist ID) S220

The method 200 includes receiving (e.g., retrieving, referencing, etc.) a radiologist ID S220, which functions to enable an impression section of the radiologist report to be determined in accordance with the radiologist's reporting language style. Additionally or alternatively, the radiologist ID can function to enable any other suitable section(s) of the radiologist report to be generated.

The radiologist ID is preferably linked to a radiologist style as described above (e.g., within the architecture of one or more models, through a lookup table, etc.) but can additionally or alternatively be otherwise associated with one or more radiologist styles. The radiologist ID is preferably assigned to a radiologist during an onboarding process (e.g., as described above, and referenced based on the name of the radiologist on the radiology report, etc.), but can additionally or alternatively be assigned upon the radiologist joining a radiology group, healthcare facility staff, and/or based on any other suitable trigger.

The radiologist ID is preferably received at a computing system configured to generate a radiology report impression section, further preferably a remote computing system, but can additionally or alternatively be received at any suitable computing system. The radiologist ID can be automatically received upon the generation of a set of radiology images, upon the initiation of the generation of a report, upon the generation and/or receipt of a set of finding inputs, upon the completion of one or more sections of a radiology report, once entered by a radiologist or other user, and/or at any suitable time based on any suitable trigger(s).

S220 can optionally include receiving any other suitable information, such as any or all of: patient information (e.g., patient age, other patient demographic information, etc.), patient history, healthcare facility information, and/or any other suitable information.

In a first variation, the radiologist ID is assigned to each radiologist upon being onboarded into the system 100, wherein the radiologist ID is associated with a particular radiologist style vector, wherein the radiologist style vector is determined and/or received at a remote computing subsystem (e.g., from remote storage, from local storage, etc.).

4.4 Method—Receiving a Set of Finding Inputs S230

The method 200 includes receiving a set of finding inputs S230, which (e.g., along with the radiologist style) functions to receive information associated with a set of radiology images with which an impression can be generated.

The set of finding inputs preferably includes the entire findings section of a radiology report, wherein the findings section is represented as a string of text, and wherein each of the set of finding inputs is a word in the string of text. Any or all of the findings section can be manually entered (e.g., typed) by a radiologist or other user, transcribed from radiologist speech (e.g., with a speech recognition program), automatically generated, and/or otherwise determined.

The method 200 can optionally include modifying the set of finding inputs, such as preprocessing the radiology report and/or findings section (e.g., removing formatting, preprocessing as described above, etc.) and/or performing any other suitable edits on the findings section and/or any other suitable sections of the radiology report.

The set of finding inputs are preferably received at a computing system (e.g., wherein the radiologist ID is received), further preferably at a remote computing system. The set of finding inputs can be received upon completion of the findings section (e.g., as determined based on radiologist input, as determined based on monitoring movement of a caret associated with a radiologist display, etc.), prior to a findings section being completed, and/or at any other suitable time(s).

In some variations, S230 includes determining when the findings section has been completed, which functions to prevent an impression section from being prematurely generated (e.g., with incomplete information). Determining this can include any or all of: checking for empty fields in the report, monitoring and/or checking for changes to the report (e.g., checking for a change from a templated entry within a field to a dictated, typed or macro-based entry within the field), or otherwise monitoring the report.

In some variations, S230 includes determining when the impression section has been or is being dictated, typed, inserted as macro text, or otherwise manually added by the radiologist, which functions to prevent an impression section from being generated with a zero-click generation process when not needed. Determining this can include any or all of: monitoring and/or checking for changes in the impression section(s) (e.g., checking for a change from a templated entry within a field to a dictated, typed or macro-based entry within the field), or otherwise monitoring the report.

In a first variation, S230 includes receiving at a remote computing subsystem the set of words collectively making up a completed findings section of the report, wherein an embedding process is performed to numerically represent the set of words.

4.5 Method—Determining a Context of Each of the Set of Finding Inputs S240

The method 200 includes determining a context of each of the set of finding inputs S240, which functions to enable the generation of an accurate, intelligible radiology impression based on the set of findings as a whole. Additionally or alternatively, S240 can function to generate an accurate, intelligible radiology impression based on any or all of: patient information, healthcare facility information, and/or any other suitable information inputs. Further additionally or alternatively, S240 can function to generate any suitable section(s) of the radiology report in an accurate, intelligible, and/or radiologist-specific manner.

The context defines the relationship of each of the set of finding inputs with the other finding inputs (e.g., surrounding findings inputs, adjacent finding inputs, all other finding inputs, etc.) of the findings section. The context of each finding input (e.g., word) can take into account any or all of: a tense of other finding inputs; a grammatical characterization of other finding inputs (e.g., noun, verb, adjective, adverb, etc.); a subject matter characterization of other finding inputs (e.g., technical word, medical word, linking word, patient condition characterization, parameter value, etc.); an ontology of any or all of the finding inputs; a length of other finding inputs; the presence of an identifier and/or signifier finding input; and/or any other feature(s) of the other finding inputs and/or the finding input itself.

The context is preferably determined with a set of models no as described above, further preferably with a model including one or more attention processes (e.g., self-attention process, during an encoding process, with a self-attention layer in an encoder, with a self-attention layer in a decoder, during an encoder-decoder attention process, etc.), such as, but not limited to, any or all of the attention processes described above. One or more of the attention processes preferably assesses (e.g., quantifies, calculates, etc.) the relationship of each of a set of finding inputs, such as each word of the text of the radiology report's findings section, to each of the other finding inputs. This can function to determine how much each finding input depends on the other finding inputs in the overall set of finding inputs (e.g., collectively forming a sentence of the findings section, collectively forming the entire findings section, etc.). Additionally or alternatively, this can function to enable the determination of an impression which takes into account multiple different findings (e.g., recommendation for a patient experiencing comorbidities); enable the ranking and/or relative importance of one or more findings, and/or perform any other suitable functions.

A set of encoders (e.g., encoding layers) are used to implement the one or more attention processes, wherein the encoders function to determine a context matrix (e.g., vector, 2-dimensional matrix, 3-dimensional matrix, etc.) associated with the finding inputs. Each of the encoders preferably includes a self-attention mechanism (e.g., self-attention layer) and a feed forward neural network, but can additionally or alternatively include any suitable architecture with any suitable neural networks (e.g., convolutional, recursive, recurrent, etc.) and/or layers (e.g., attention layers). Any or all of the encoders preferably receive as an input a set of word embedding vectors and/or one or more word embedding matrices (e.g., as determined with an embedding algorithm, as determined with the first encoder, a 512-dimensional word embedding vector for each word, etc.), which characterizes the text of the findings section. Additionally or alternatively, any or all of the encoders can receive any other representation of the set of findings inputs (e.g., text itself) and/or any other suitable information as inputs. In some variations, for instance, the matrix includes one or more auxiliary fields, such as any or all of: the radiologist style matrix, other radiologist information, patient information, radiology group and/or healthcare facility information, and/or any other suitable information. In specific examples, for instance, the radiologist style matrix is concatenated with a word embeddings matrix and/or each of a set of word embedding vectors and processed by a set of encoders to determine the context matrix. Further additionally or alternatively, any or all of this information can be received separately (e.g., in another matrix); received at another time in the method 200 (e.g., radiologist style matrix is concatenated with the context matrix later in the method 200); received at multiple processes in the method; not received; and/or otherwise received.

The set of encoders preferably additionally receives and/or determines a set of positional encodings, which functions to enable the order of the words in the findings section to be taken into account for determining context. In variations involving a transformer model, for instance, in which processing of the finding inputs is performed at least partially in parallel, a positional encoding associated with each of the finding inputs is preferably used to enable order (e.g., position of the finding input within the findings section) to be taken into account when determining context.

S240 can optionally include running an information extractor over the finding inputs and using the results as input to the set of encoders (e.g., as an auxiliary field, with the set of word embeddings, with the set of word embeddings and positional encoder, etc.). The information extractor preferably functions to determine any concepts associated with the set of finding inputs, such as concepts as determined by one or more ontology databases (e.g., clinical ontology database). In a first set of variations, for instance, an ontology database is used to determine a set of concept identifiers [IDs] associated with the set of finding inputs (e.g., a subset of the finding inputs), wherein the concept identifiers can be used as any or all of: a separate input (e.g., table, matrix, vector, etc.) relative to the word embeddings; an input with the word embeddings (e.g., concatenated with the word embeddings and/or a word embedding matrix); and/or otherwise received as an input to a set of encoders. Additionally or alternatively, an ontology databased can be used during a training of one or more models. In some variations, for instance, associating words of the impression fields of training data with concepts in the ontology data-based can be used to better train the models, be used in inference, and/or be used in any other suitable ways.

Extracting information to be used in S240 can optionally include detecting negation, which refers to findings that indicate something (e.g., a condition) is not there. For instance, a finding which indicates that the patient's heart is "not enlarged," the negation "not" can be indicated in and/or associated with the relevant word embedding(s). In some examples, an auxiliary field is added and/or associated with the word embeddings to indicate which finding inputs are associated with a negation, thereby increasing an accuracy of the resulting impression. In examples further including extracting information from an ontology database, this can help look for appropriate concepts (e.g., normal sized heart concepts). Additionally or alternatively, negation can be otherwise implemented and/or S240 can include any other suitable processes and/or absence of a negation detection process.

In a set of specific examples, S240 includes determining a set of concept IDs, which are words, associated with particular finding inputs with an ontology database and determining embeddings for the concept IDs in a separate embedding table and/or matrix and/or vector; adding a token type to the word embeddings and the concept ID embeddings (e.g., a token type of "o" for words and a token type of "1" for concepts); and concatenating the word embeddings and the concept embeddings. The concatenated matrix further preferably includes and/or is determined based on positional encodings of the embeddings, so that the finding word associated with the particular concept are aligned. Additionally or alternatively, determining and using the concept IDs can be otherwise performed.

Additionally or alternatively, the information extractor can determine any other suitable information.

S240 preferably produces one or more of the following as an output: a single context matrix (e.g., context vector, matrix formed from multiple context vectors, matrix formed from multiple context matrices, etc.); multiple context matrices (e.g., set of multiple context vectors, a context matrix for each finding input/word embedding); any other matrices and/or parameter values (e.g., confidence score); and/or any combination of matrices and/or values. Additionally or alternatively, S240 can produce output relating and/or corresponding to concepts from one or more ontology databases (e.g., clinical ontology database). Additionally or alternatively, S240 can produce any other suitable outputs and/or combination of outputs.

In some variations, for instance, the context of each finding input is represented in a matrix or vector which includes a set of values indicating the dependence of the finding input on each of a set of surrounding finding inputs. The surrounding findings inputs can collectively include the other words in the sentence in which the finding input word is placed, all other words in the findings section, and/or any other suitable words in any suitable section of the radiology report.

Additionally or alternatively, determining the context can include any other suitable processes, such as any or all of: eliminating finding inputs (e.g., based on low dependency of other finding inputs on the specific finding input, based on the determination of a redundant finding input, etc.), referencing other sections of the report, referencing the radiologist style, updating and/or otherwise altering the radiologist style, and/or otherwise determining the context of the finding inputs.

In a first variation, a context matrix is determined with a set of encoders (e.g., 6 encoders, 7 encoders, 8 encoders, 9 encoders, 10 encoders, 11 encoders, 12 encoders, between 12 and 15 encoders, between 5 and 10 encoders, between 10 and 15 encoders, greater than 15 encoders, etc.) in an encoder-decoder architecture of a transformer model. In specific examples, determining a context of each of the set of finding inputs includes, at self-attention layers of the encoders, calculating a set of context values for each finding input, wherein set of context values quantifies how much the finding input depends on each of the surrounding finding inputs. The context matrix is preferably determined based on a set of word embeddings, each of the set of word embeddings associated with a word of a findings section. The word embeddings can optionally be concatenated with and/or otherwise associated with (e.g., in a separate matrix) other information (e.g., forming auxiliary fields of a concatenated matrix), such as, but not limited to, any or all of: concepts associated with any words of the findings section (e.g., as determined using an ontology database); positional encodings; negations; and/or any other suitable information.

4.6 Method—Determining an Impression Based on the Context and the Radiologist Style S250

The method 200 includes determining an impression based on the context and the radiologist style S250, which functions to automatically fill in an impression field of a radiology report. Additionally or alternatively, S250 can function to mimic the particular style (e.g., length, level of detail, word choice, content of recommendations and/or follow-up steps, etc.) of a radiologist; determine an accurate impression based on a set of findings; enable the determination of tunable (e.g., in length, detail, time required to generate, etc.) impression field; and/or perform any other function(s).

The impression (which equivalently refers to herein any or all of: a single impression, a sentence of an impression section, the entire impression section, and/or any other suitable portion and/or feature of the impression section of a radiology report) is preferably generated on a word-by-word basis through a set of one or more decoding processes, wherein a set of the decoders determine each word of the impression. The set of decoders preferably determines each word by selecting it from a set of potential words based on a probability score assigned to each of the set of potential words. The probability score is further preferably calculated based on the context values (e.g., in the form of a set of context value vectors, in the form of a context value matrix, etc.) associated with each of the set of finding inputs, along with the set of radiologist style coefficients (e.g., in the form of a radiologist style vector, in the form of a radiologist style matrix, etc.).

S250 preferably includes concatenating the radiologist style matrix (e.g., radiologist style vector) with the context matrix, wherein the concatenated matrix is processed in S250 (e.g., in a set of decoders as described below). The context values and the radiologist style values can be concatenated together in any or all of the following: into a single vector for each finding input, into a matrix for each finding input, into a matrix for all finding inputs, and/or otherwise combined. Additionally or alternatively, the radiologist style matrix and the context matrix can do any or all of: remain in separate vectors and/or matrices, be used in the determination of a new vector or matrix, and/or be otherwise associated or independent.

The set of potential words for each word entry in the impression field is preferably determined based on a set of neural networks (e.g., feed forward neural networks) within a set of decoders (e.g., decoder layers). The decoders are preferably part of an encoder-decoder architecture of a transformer (e.g., multi-transformer) model, but can additionally or alternatively be integrated within any suitable model(s). The set of decoders can include any suitable number of layers (equivalently referred to herein as number of decoders), such as any or all of: between 1 and 6 (e.g., 1, 2, 3, 4, 5, 6), between 6 and 12 (e.g., 6, 7, 8, 9, 10, 11, 12), greater than 12 (e.g., 13, 14, 15, 16, etc.), between 15-20 (e.g., 15, 16, 17, 18, 19, 20), greater than 20 (e.g., 25, 30, 35, etc.), and/or any suitable number. In some variations, the number of decoders or number of layers within a decoder is reduced (e.g., relative to conventional decoders) to speed up the processing (e.g., a beam search process as described below) of the decoders. In specific examples, for instance, a conventional 12-layer decoder is reduced to 6 layers to speed up a beam search process.

The set of decoders can optionally include an odd number of layers (e.g., in a standard attention process of a transformer model). Alternatively, the set of decoders can optionally be even, which can function, for instance, to enable global context attention. In specific examples, this can lead to more accurate results.

Each of the decoders in the set of decoders preferably includes a self-attention mechanism (e.g., self-attention layer), an attention mechanism (e.g., attention layer over the encodings), and a feed forward neural network. Additionally or alternatively, any or all of the decoders can have any suitable architecture including any number and type of layers, any neural network (e.g., convolutional, recursive, recurrent, etc.) and/or combination of neural networks, an absence of one or more layers and/or neural networks, and/or any combination of components.

S250 can additionally or alternatively include any number of additional processes, such as an encoding process, a normalization process, and/or any other suitable process(es).

The impression section is preferably determined on a word-by-word basis, such as one word at a time in a sequential fashion. Additionally or alternatively, any or all of the words can be determined in parallel and/or in other non-sequential fashion; a single pass decoding (e.g., non-auto-regressive decoding) process can be implemented to decode the whole sequence and/or a portion of the sequence at one time (e.g., to increase the speed of processing; and/or the impression text can be determined in any suitable way and/or time(s).

Determining the impression preferably includes determining and assigning probability scores (e.g., with the neural networks of the decoders, with a separate neural network, with a separate feed forward neural network, etc.) to potential words of the impression (e.g., generating the impression text one word at a time), wherein the selected words are associated with the highest probability scores (e.g., relative to the other words being considered for that position in the impression text). Additionally or alternatively, the impression can be any or all of: generated in absence of probability scores (e.g., with a ranking and/or prioritization of words); generated with manual input (e.g., from a radiologist); generated with random selection of one or more words; and/or generated in any other suitable way(s).

In a preferred set of variations, probability scores are determined and/or used in accordance with a beam search decoding process to determine the text of the impression. The beam search decoder is preferably associated with and/or assigned a particular beam width value (e.g., 2, 3, 4, 5, 6, 7, 8, 9, 10, between 2 and 5, between 5 and 10, greater than 10, etc.), wherein the beam width corresponds to (e.g., is equal to, is related to, etc.) the number of words considered at each position. Additionally or alternatively, any other suitable process can be used (e.g., Greedy Search algorithm) in selecting the words for the impression text.

In a specific example, for instance, a beam width of the beam search process is equal to three, wherein each word of the impression is selected from a set of three potential words, each assigned a probability score based on the set of context values and the radiologist style values. The output of the beam search process is preferably a most probable sequence of words, which forms the impression text. Determining the most probable sequence preferably includes routinely terminating least probable paths based on the probability scores determined at each potential word calculation, but can additionally or alternatively include any other processes (e.g., elimination processes). Further additionally or alternatively, the beam width can have any suitable value (e.g., less than three, greater than three, etc.).

S250 can optionally include performing a length prediction process, which functions to predict the length that the impression would be (e.g., if manually generated by the particular radiologist, based on an aggregated set of radiologists, based on the findings, etc.), and produce an impression based on the predicted length. In decoding processes, for instance, the length of the output can be chosen, designed, and/or tuned. In some variations, for instance, a training of the set of models includes learning how long an impression generally is based on the length of the impression field in the training data (e.g., manually generated radiology reports, synthetic radiology reports, etc.), which can then be used to prescribe the length of the automatically generated impression. A length prediction module used to perform the length prediction can be any or all of: part of the model performing the decoding; part of a separate model (e.g., separate than the model performing the encoding and/or decoding, separate from a transformer model, etc.); and/or part of any suitable models. The length prediction module can receive a radiologist ID and/or radiologist style as an input. Additionally or alternatively, the length prediction module can receive any other suitable input(s).

In some variations of S250, one or more parameters of the impression field are tunable, such as any or all of: length, level of detail, comprehensiveness (e.g., number of findings commented upon), and/or any other suitable parameters. In some examples, for instance, a parameter associated with a length of the impression section (e.g., quantifying the length, number of words, level of detail, etc.) is tunable by any or all of: a particular radiologist, a radiology group, a healthcare facility, and/or any other suitable entities or combination of entities. In specific examples, a parameter alpha, which is an exponent that weights the scores returned out of a beam search decoding process, is able to be adjusted by a radiologist or by a radiology group, wherein a smaller value of alpha returns an impression faster but at a shorter length and/or lesser level of detail, whereas a larger value of alpha returns an impression slower but at a longer length and/or greater level of detail. Additionally or alternatively, any other suitable parameters can be tunable at any suitable processes of the method (e.g., in S240).

In a first variation of S250, S250 includes performing a decoding process of the outputs determined in S240 (e.g., with one or more encoders of S240), wherein the decoding process includes a beam search process performed with a set of decoder layers (e.g., 6, 12, etc.), wherein the impression text is generated on a word-by-word basis based on a probability associated with each of a set of word options as prescribed by the beam width of the beam search decoder(s), the probabilities determined based on one or more context matrices and one or more radiologist style matrices.

4.7 Method—Inserting the Impression into the Report S260

The method 200 includes inserting the impression into the radiology report S260, which functions to complete the impression section of the radiology report. Additionally or alternatively, S260 can function to perform any or all of: concluding (e.g., automatically concluding) the generation of a radiology report; triggering a next action (e.g., uploading the radiology report to a database, transmitting the radiology report to another entity such as a physician treating the patient and/or a clinical care team, notifying the radiologist that the report has been completed, prompting a radiologist to review and/or edit the impression section, etc.); requiring zero clicks from the radiologist to insert the impression text; establishing integration with one or more radiology software platforms; and/or performing any other suitable function(s).

S260 is preferably performed with zero clicks (e.g., no required hotkeys, no input from the radiologist, no mouse clicks, no keyboard clicks, etc.), but can additionally or alternatively be performed with one click, multiple clicks, the press of keyboard hotkey(s) or button on a dictation or navigation device, and/or based on any other input(s) and/or trigger(s) (e.g., from a radiologist). Insertion can be performed with and/or include any or all of: injection; user interface automation; copy and paste; and/or any other suitable processes. The way in which the impression is inserted is preferably determined based on the particular software program and/or particular radiology platform being implemented. Additionally or alternatively, an impression can be otherwise integrated within the radiology report and/or require any number of inputs and/or clicks (e.g., single click).

S260 can include any number of processes and/or detection of features for determining the appropriate location at which to insert the impression text (e.g., to insert the text in the proper location, to prevent overriding of other sections, etc.), since this location (e.g., and type of box such as RTF edit box, etc.) can vary depending on the radiology platform being used (e.g., Fluency vs. PowerScribe). These processes preferably include invisibly monitoring the location of a caret (e.g., cursor) within the radiology report document, and determining the appropriate location of the impression field based on navigation of the caret (e.g., as shown in FIGS. 3A-3D). In some variations, for instance, the impression section is detected based on detecting one of a variety of impression headers, and by characterizing the text that follows the impression section (e.g., a call report/critical value sentence; a different section header in the case of reports with different arrangements of findings vs. impressions, etc.), and determining where the caret is in relation to these headers and other text.

In additional or alternative variations, it is known that the impression field is usually located at the end of the report, so a determination that there is a header denoting the impression section prior to the caret and no text in front of the caret indicates that the caret is likely in the impression field, and can thereby trigger the insertion of impression text.

The trigger for entering the impression text in the impression field can include detecting that a caret has entered into the impression field; additionally or alternatively, the impression text can be inserted based on a different trigger, based on multiple triggers, in absence of a trigger, otherwise, and/or based on any combination of these.

Figure 5:
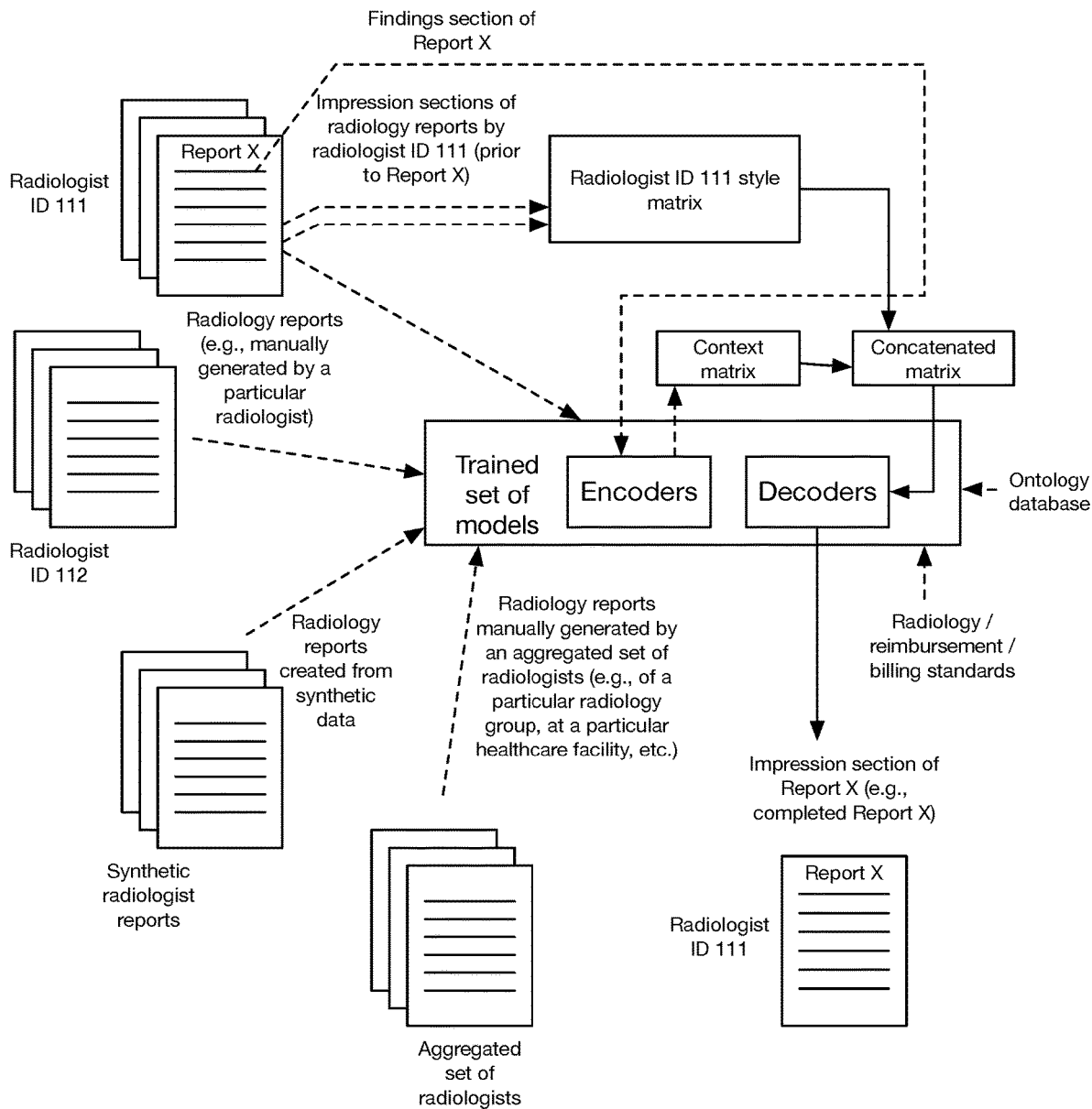
FIG. 5 depicts a schematic variation of the inputs and outputs in a system and/or method for the automated generation of impression text in a radiology report.

A variation of the information used to train the set of models, process the set of models, determine impression text, and insert impression text is shown in FIG. 5.

5. Variations

In a first variation of the system 100 (e.g., as shown in FIG. 4), the system includes: a set of models 110, wherein the set of models includes a transformer model including a set of encoders and set of decoders, the set of decoders including one or more beam search decoders, wherein the set of encoders receives the radiologist style matrix and the set of findings from the findings section of the radiologist report to determine a context matrix, which is used by the beam search decoder to automatically generate the impression section. The system interfaces with a radiology platform including a speech recognition platform, wherein the speech recognition platform can be used to provide the findings section to the system, receive the automated impression and insert it into the report, and/or be otherwise integrated with and/or in communication with the system. The system 100 can additionally include any other suitable components, such as any or all of: a preprocessing module (e.g., as described above), a post processing module (e.g., as described above), a computing system, and/or any other suitable components and/or combination of components.

In a first variation of the method 200, the method includes any or all of: during an onboarding process of a radiologist, determining a radiologist style matrix (e.g., vector) based on a set of multiple (e.g., at least 100; at least 300; at least 1,000; at least 10,000; between 1,000 and 100,000; at least 100,000; at least 200,000; etc.) manually-generated radiology reports completed by the radiologist, wherein the radiologist style matrix includes a set coefficients defining the radiologist's style (e.g., word choice, word flow, length, summary of multiple findings, prioritization of findings, etc.) in generating impression text of the radiologist report; upon a trigger indicating that a report is to be generated and/or is in the process of being generated by the radiologist, receiving a radiologist ID at a remote computing system (e.g., upon initiation of the associated radiology report, upon detecting that a subset of sections of the report have been completed, upon detecting that the findings section of the report has been completed, upon input from a radiologist, etc.), wherein the radiologist style matrix is associated with the radiologist ID (e.g., within the architecture of the models, in a cloud-based lookup table, etc.); receiving a set of finding inputs from a findings section of the radiologist report (e.g., upon detecting that the findings section has been completed, upon detecting that all sections besides the impression section have been completed, upon receipt of the radiologist ID, etc.) at the remote computing system, wherein each of the finding inputs is an identifier (e.g., numeric identifier) corresponding to a word of the string of words making up the findings section; determining a set of one or more context matrices associated with the finding inputs (e.g., a context matrix for each finding input) with a set of one or more attention process(es) (e.g., attention layer in an encoder, attention layer in a decoder, etc.), wherein the context matrix defines the relationship between the finding input and the other finding inputs of the collective findings section; determining a set of first word options and associated probabilities based on the radiologist style and the context (e.g., in a concatenated matrix, in a concatenated vector, etc.); repeating this for subsequent words; generating a string of words for the impression text with a beam search process (e.g., beam search decoder) based on these probabilities; and inserting the impression text into the radiology report (e.g., based on detecting one of a variety of impression headers, characterizing the text that follows the impression section, and determining where the caret is in relation to these headers and other text; based on a trigger indicating that the radiologist has entered the impression section and that a cursor is arranged in a field with no subsequent text; etc.). The method can optionally additionally include receiving patient information (e.g., with the radiologist ID), such as a patient age; receiving healthcare facility and/or radiologist organization information (e.g., with the radiologist ID), such as an organization code; and/or receiving any other metadata associated with generating a radiology report; performing pre-processing of any or all of the input(s); and/or any other process(es).

Additionally or alternatively, the method 200 can include any or all of: training the set of models (e.g., based on manually generated radiology reports, based on synthetic radiology reports, based on the information shown in FIG. 5, etc.); performing one or more preprocessing processes (e.g., removing or modifying formatting, false positives, and/or false negatives for the radiology reports being used in training); performing one or more postprocessing processes (e.g., checking the impression text for words in compliance and/or not in compliance with one or more standards, alerting the radiologist to words or phrases not in compliance with one or standards, replacing words or phrases not in compliance with one or more standards, etc.); receiving an input regarding a tunable parameter (e.g., length of impression section, level of detail, etc.) from the radiologist and adjusting the impression section (e.g., generating a new impression section) based on the parameter value; referencing an ontology database to determine concept associated with the set of findings; embedding the concepts as auxiliary fields in a matrix including word embeddings associated with the findings, wherein the concepts and findings are linked based on positional encodings; and/or any other suitable processes performed in any suitable order.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
    training a machine learning model based on a first set of historical radiology reports, wherein the machine learning model comprises a transformer model comprising a set of encoders and a set of decoders;
    tuning the machine learning model based on a second set of historical radiology reports, wherein the second set of historical radiology reports are associated with a radiologist, wherein tuning the machine learning model comprises learning a writing style for the radiologist, the writing style reflecting at least one of: a length metric, a word choice, an ordering style, or a summarization style;
    determining a set of finding inputs for a radiology report associated with a patient;

using the set of encoders of the tuned model, determining a set of embeddings based on the set of finding inputs, and determining a context matrix based on the set of embeddings;

using the set of decoders of the tuned model, generating an impression section of the radiology report based on the radiologist style matrix and the context matrix, wherein the impression section is configured to mimic the writing style for the radiologist;

retraining the machine learning model based on the generated impression section of the radiology report to determine a retrained model; and with the retrained model, generating a second impression section of a second radiology report.

2. The method of claim 1, further comprising receiving patient information for the patient, wherein the context matrix is further determined based on the patient information.

3. The method of claim 2, wherein the patient information comprises at least one of: patient history, patient demographic information, or information from a prior radiology report for the patient.

4. The method of claim 1, further comprising receiving healthcare facility information associated with the patient, wherein the context matrix is further determined based on the healthcare facility information.

5. The method of claim 1, further comprising
determining a clinical recommendation based on consensus guidelines and the finding inputs; and
outputting a notification at a radiologist interface based on the clinical recommendation.

6. The method of claim 1, further comprising providing a tunable parameter at an interface, wherein the impression section is automatically adjusted based on the tunable parameter, wherein the tunable parameter comprises at least one of: a level of detail, a length metric, an ordering style, or a summarization style.

7. The method of claim 1, wherein generating the impression section of the radiology report comprises automatically inserting the generated impression section with a zero-click insertion process.

8. The method of claim 1, wherein at least a subset of the set of finding inputs are predicted based on a set of images, using a second model.

9. A system, comprising:
a computing system configured to:
train a machine learning model based on a first set of historical radiology reports, wherein the machine learning model comprises a transformer model comprising a set of encoders and a set of decoders;
tune the machine learning model based on a second set of historical radiology reports, wherein the second set of historical radiology reports are associated with a radiologist, wherein tuning the machine learning model comprises learning a writing style for the radiologist, the writing style reflecting at least one of: a length metric, a word choice, an ordering style, or a summarization style;

determine a radiologist style matrix using the tuned machine learning model;
determine a set of finding inputs for a radiology report associated with a patient;
use the set of encoders of the tuned model to determine a set of embeddings based on the set of finding inputs, and determine a context matrix based on the set of embeddings;
use the set of decoders of the tuned model to generate an impression section of the radiology report based on the radiologist style matrix and the context matrix, wherein the impression section is configured to mimic the writing style for the radiologist;
retrain the machine learning model based on the generated impression section of the radiology report to determine a retrained model; and
with the retrained model, generate a second impression section of a second radiology report.

10. The system of claim 9, wherein the computing system is further configured to:
determine a clinical recommendation based on consensus guidelines and the set of finding inputs; and
output a notification based on the clinical recommendation.

11. The system of claim 9, wherein the computing system is further configured to:
using a second trained model, check the impression section of the radiology report; and
output a notification in response to checking the impression section.

12. The system of claim 11, wherein checking the impression section of the radiology report comprises checking for compliance between the impression section and at least one of: billing guidelines or merit-based incentive payment system (MIPS) guidelines.

13. The system of claim 9, wherein the computing system is further configured to
reference an ontology database to determine a set of concepts associated with the set of finding inputs; and
wherein the context matrix is further determined based on the set of concepts.

14. The system of claim 9, wherein the computing system is further configured to interface with a database, wherein the database comprises at least one of: a Picture Archiving and Communication System (PACS), an electronic medical record (EMR) database, an electronic health record (EHR) database, or a Radiology Information System (RIS).

15. The system of claim 14, wherein the computing system is further configured to receive patient information from the database, wherein the text for the impression section is further generated based on the patient information.

16. The system of claim 14, wherein the computing system is configured to transmit information to the database based on the radiology report, in response to detecting completion of the radiology report.

* * * * *

UNITED STATES PATENT AND TRADEMARK OFFICE
CERTIFICATE OF CORRECTION

PATENT NO. : 11,915,809 B2
APPLICATION NO. : 18/207880
DATED : February 27, 2024
INVENTOR(S) : Jeffrey Chang et al.

It is certified that error appears in the above-identified patent and that said Letters Patent is hereby corrected as shown below:

In the Claims

Column 23, Line 27, In Claim 5, after "comprising", insert --:--

Column 24, Line 39, In Claim 13, after "to", insert --:--

Signed and Sealed this
Sixteenth Day of April, 2024

Katherine Kelly Vidal
Director of the United States Patent and Trademark Office